United States Patent [19]

Shigeta et al.

[11] Patent Number: 4,800,887
[45] Date of Patent: Jan. 31, 1989

[54] X RAY-TRANSPARENT ELECTRODE FOR A LIVING BODY

[75] Inventors: Masatomo Shigeta; Hikonori Abe; Shinichi Nishiyama, all of Iwaki, Japan

[73] Assignee: Kureha Kagaku Kogyo Kabushiki Kaisha, Tokyo, Japan

[21] Appl. No.: 900,661

[22] Filed: Aug. 26, 1986

[30] Foreign Application Priority Data

Aug. 27, 1985 [JP] Japan ................................ 60-187596

[51] Int. Cl.⁴ .......................... A61B 5/04; A61N 1/04
[52] U.S. Cl. ..................................... 128/639; 128/798; 128/803
[58] Field of Search ............... 128/639–641, 128/643, 644, 783, 798, 802, 803, 784–786, 419 P

[56] References Cited

U.S. PATENT DOCUMENTS

| | | | |
|---|---|---|---|
| 3,722,005 | 3/1973 | Cowland | 128/642 X |
| 4,102,331 | 7/1978 | Grayzel et al. | 128/640 |
| 4,198,991 | 4/1980 | Harris | 128/784 |
| 4,248,237 | 2/1981 | Kenny | 128/419 P |
| 4,417,581 | 11/1983 | Dawson | 128/639 |

FOREIGN PATENT DOCUMENTS

| | | | |
|---|---|---|---|
| 1388870 | 10/1971 | Australia | 128/798 |
| 122258 | 2/1972 | Denmark | 128/641 |

Primary Examiner—Lee S. Cohen
Attorney, Agent, or Firm—Armstrong, Nikaido, Marmelstein & Kubovcik

[57] ABSTRACT

An electrode for a living body comprises a main body consisting of a flexible sheet of graphite and the whole of the electrode is made substantially transparent in regard to X rays so that the electrode is not a hindrance to an X-ray inspection.

4 Claims, 3 Drawing Sheets

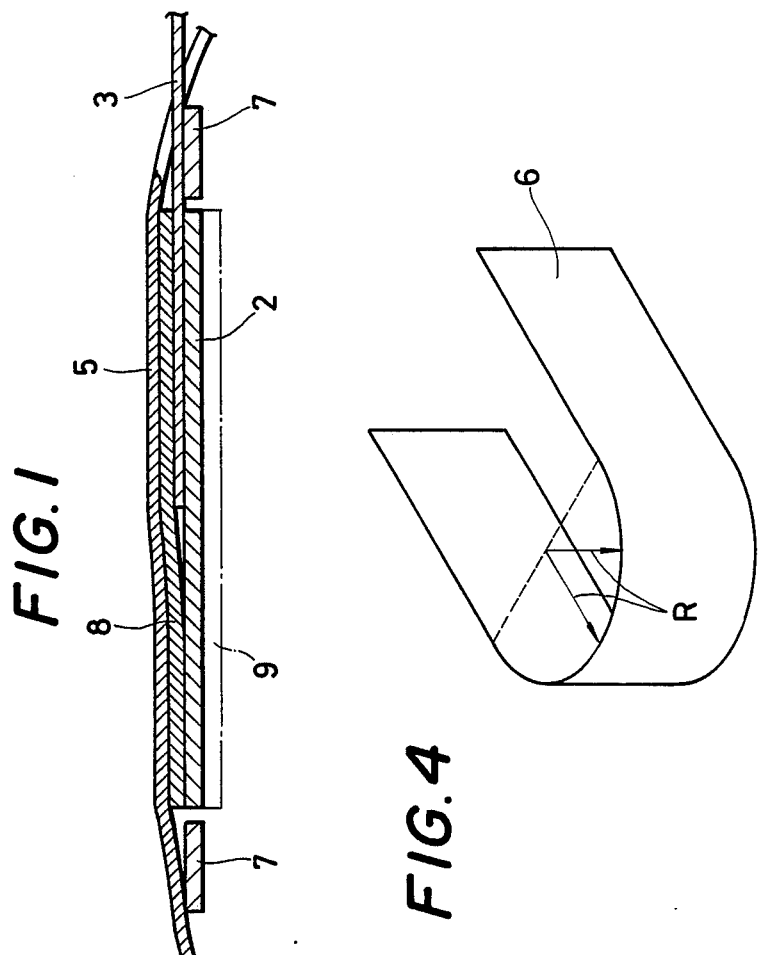

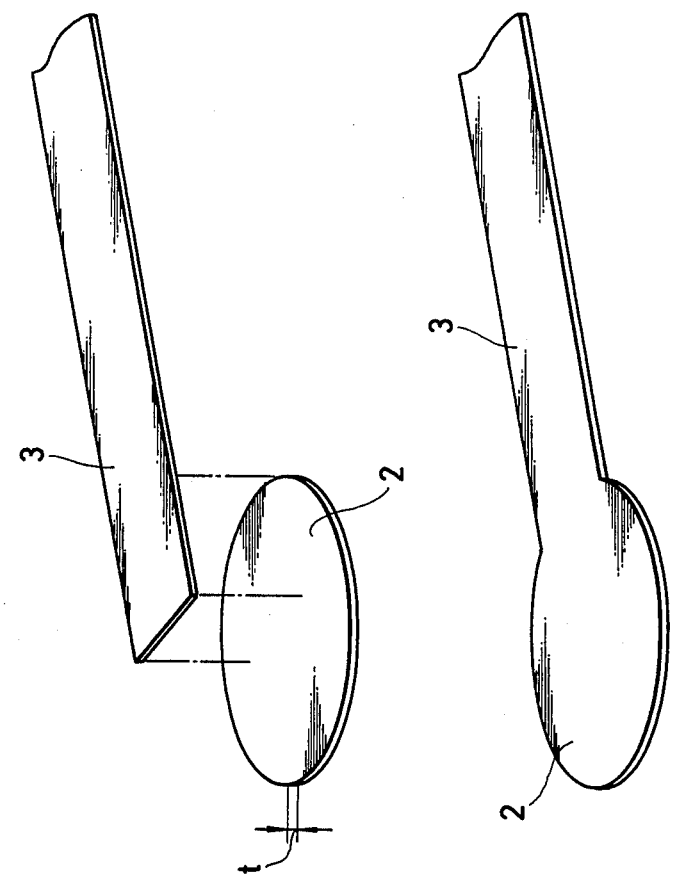

X RAY-TRANSPARENT ELECTRODE FOR A LIVING BODY

BACKGROUND OF THE INVENTION

1. Field of the Invention:

This invention relates to an electrode for a living body which is suitable for a defibrillator, an electrocardiograph, or the like.

2. Description of the Prior Art:

In the process of a cardiac catheterization, a catheter is inserted into a blood vessel of a patient to inject a contrast media for X-ray inspection. There is, however, the case that the patient's heart is convulsed for more than 15 to 30 seconds due to an excitation in the middle of the inspection. If the convulsion of the heart continues for a long time, it causes damage to brain cells through interruptions of blood flow. Accordingly, when such a convulsion of the heart arises, in general, a high-voltage shock of 3000 to 5000 volts is given to the heart with a defibrillator.

Such a conventional defibrillator has generally a box-shaped body provided with a handle at the upper surface of the body. The defibrillator is provided with electrodes at the lower surface of the body. The electrodes are to be brought into contact with a patient's body at the portion over his heart to give an electric shock to the heart.

Such a conventional defribrillator is, however, very troublesome because it must be brought out to be used whenever the patient's heart is convulsed. Especially, there is the possibility that it is not in time for the case of emergency.

Besides, on several occasions, the electrodes of an electrocardiograph must be attached to the surface of a patient's body for getting electrocardiograms at the time of an X-ray inspection. But, because the electrodes of such an electrocardiograph are conventionally made of metal and they are not transparent in regard to X rays, they are hindrances to X-ray photographing.

SUMMARY OF THE INVENTION

Accordingly, it is an object of the present invention to provide an electrode for a living body which is substantially transparent in regard to X rays so as not to hinder any X-ray inspection.

It is another object of the present invention to provide an electrode for a living body which can serve both as electrodes of an electrocardiograph and a defibrillator.

It is still another object of the present invention to provide an electrode which can closely contact with any living body.

The above and other objects can be attained by the present invention as follows. An electrode has a main body consisting of a flexible sheet of graphite, at least the surface of the electrode to contact with a living body is made flexible, and the whole of the electrode is made substantially transparent in regard to X rays.

Other and further objects of the invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF DRAWINGS

FIG. 1 is a cross-sectional view showing an electrode of a defibrillator according to an embodiment of the invention;

FIGS. 2A and 2B are perspective views of electrodes with lead portions;

FIG. 4 is a perspective view for illustrating the flexibility of a graphite sheet.

DETAILED DESCRIPTION OF THE PREFERRED EMBODIMENTS

Hereinafter, embodiments in which the present invention is applied to the electrodes of a defibrillator will be described with reference to attached drawings.

Figure 3A:
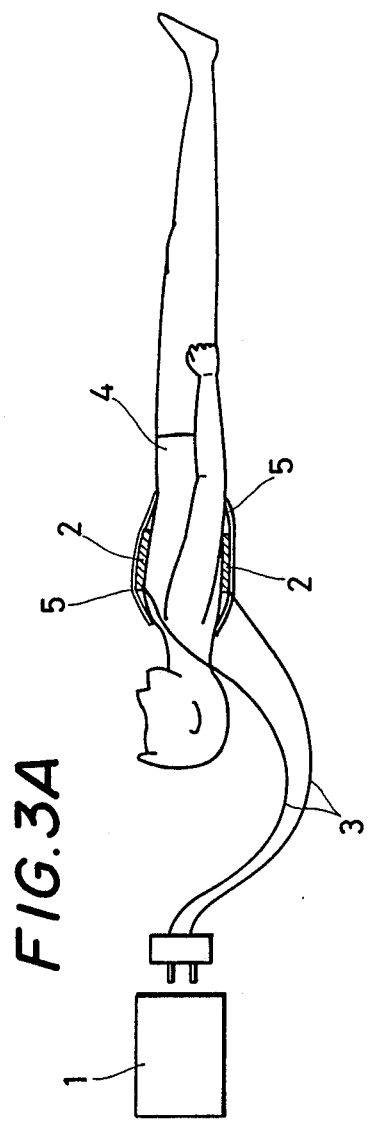
FIGS. 3A and 3B are a side view and a plan view showing a manner of use of the defibrillator.
Figure 3B:
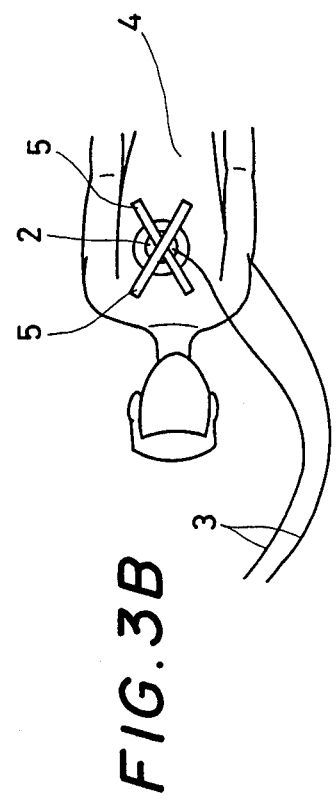

Referring first to FIGS. 3A and 3B, defribrillator comprises a high-voltage source 1, a pair of electrode body (hereinafter, each merely called "electrode") 2, and leads 3 for connecting the electrodes to the high-voltage source. Each electrode 2 consists of a disk-like flexible sheet (see FIGS. 2A and 2B) having the area of about 50 cm and the thickness of about 0.1 to 2 mm. The electrodes 2 are attached to a patient's body 4 from both of the breast side and the back side of his heart, respectively. As shown in FIGS. 1, 3A and 3B, each electrode 2 is directly attached to the patient's skin with a proper adhesive and fixed with adhesive tapes or bands 5. As the present case, when the electrodes serve as that of a defibrillator, they must be fixed in an especially firm manner because they are apt to come off from the patient's body due to a high-voltage shock.

Referring to FIG. 1, a ring-shaped sponge 7 is arranged around the electrode 2. A protective layer 8 is disposed on the upper surface of the electrode 2. As shown by imaginary lines in FIG. 1, a buffer 9 such as a sponge containing physiological sodium chloride solution may be interposed between the electrode 2 and a living body in order to improve the affinity with and the followability to the living body and the absorbability of a high-voltage shock.

Each electrode 2 is made of a crystalline flexible sheet of graphite obtained by treating natural graphite particles with concentrated sulfuric acid of 98%. For example, it can be made of Grafoil (trade name) available by Union Carbide Corp.

The thickness t of the electrode 2 preferably falls within the range of 0.1 to 2 mm, more preferably within the range of 0.2 to 1 mm. If the thickness t is less than 0.1 mm, the mechanical strength of the electrode decreases, while, if the thickness t is more than 2 mm, the flexibility of the electrode decreases.

As shown in FIG. 4, the flexibility of a graphite sheet 6 to be used as an electrode can be represented by the permissible minimum radius R of curvature when the sheet is bent. In the present invention, the radius R is preferably less than 100 mm, more preferably less than 50 mm. If the radius R is more than 100 mm, the flexibility required can not be obtained so the followability to a living body lowers and the manner of contact with the living body becomes bad. As the result, the electrode become easy to come off from the living body by a high-voltage shock or the like.

In addition, particularly in the case of the electrodes of a defibrillator, since a high voltage (3000 to 5000 volts) is applied to and a large current flows through them, the electrical resistance of each electrode is preferably less than 1.0 ohm. If the resistance is too large, the electrode may cause a burn on a living body due to the generation of heat.

Each lead 3 of the defibrillator may be made of a graphite sheet such as Grafoil, similarly to the electrode 2. FIGS. 2A and 2B show examples wherein the lead 3 is made of Grafoil. In the example shown in FIG. 2B, the electrode 2 and lead 3 are formed into one body.

Grafoil can be easily formed into any shape by punching or the like so it is superior in mass productivity. In addition, Grafoil can make the contact resistance between the lead and the electrode decrease to a value which may be disregarded.

The electrode 2 and the lead 3 can be bonded to each other with an electroconductive adhesive in which a powder of carbon black is mixed in a thermosetting resin. The thermosetting resin usable is, for example, phenolic resin, epoxy resin, etc. The content of carbon black is preferably 30 to 90 wt. %. If the content of carbon black is too little, the electrical cnductivity required can not be obtained, while, if the content is too much, the adhesive strength decreases.

Also an electroconductive adhesive wherein powder of carbon black mixed in a rubber adhesive can be used. In that case, either a natural rubber adhesive or a synthetic rubber adhesive can be used. The content of carbon black is preferably 30 to 90 wt.% from the same reason as described above. An electroconductive adhesive of this type can make the connecting portion between the electrode and the lead flexible though the adhesive strength may decrease.

Alternatively, the following method can be employed for connecting the electrode 2 and the lead 3 to each other. This is, after the electrode 2 and the lead 3 are connected to each other with an adhesive in which powder of carbon black is mixed in a thermosetting resin, the connecting portion is calcined and carbonized under a reduced pressure or in an inert atmosphere at a temperature not less than 1000° C. By this method, the electrical resistance of the connecting portion decreases to a value which may be disregarded. The thermosetting resin usable for this method is, for example, phenolic resin, epoxy resin, etc. The content of carbon black is preferably less than 90 wt. %. If the content of carbon black is too much, the adhesive strength decreases.

In the above-mentioned configuration, both of the electrodes 2 and the leads 3 are substantially transparent in regard to X rays. Therefore, they are not hindrances to X-ray photographing. As a result, the electrodes can be attached to a patient's body during an X-ray inspection.

In the present invention, also a lead made of carbon fibers can be used. In that case, however, the connecting manner of the lead to an electrode may become difficult. In addition, there are disadvantages that the electrical resistance increases and the lead becomes bulky. The above-mentioned lead 3 of Grafoil can solve all of those problems.

In the above-mentioned embodiments, the present invention is applied to the electrodes of a defibrillator. The present invention, however, can be applied also to the electrodes of an electrocardiograph. In addition, an electrode of the present invention can serve both as electrodes of a defibrillater and an electrocardiograph. Furthermore, the present invention can be applied to various electrodes such as that of an electroencephalograph and so on.

In the present invention, the main body of an electrode consists of a flexible sheet of graphite and the whole of the electrode is substantially transparent in regard to X rays. Therefore, the electrode is not a hindrance to X-ray photographing. As the result, it can be applied to the electrodes of an electrocardiograph or a defibrillater attached to a living body during an X-ray inspection. In addition, in the present invention, since the surface of an electrode to contact with a living body is made flexible, the followability to the living body is superior so the electrode is hard to come off from the living body even when it is used as an electrode of a defibrillator.

What is claimed is:

1. An electrode for a living body comprising:
    an electrode main body, at least a portion of said main body having a surface for contact with a living body being made flexible;
    a lead member for connecting said electrode main body to a electric source;
    said electrode main body and said lead member each being made of crystalline flexible graphite sheet obtained by treating natural graphite particles with concentrated sulfuric acid, each said flexible sheet having a thickness in the range of 0.1 to 2.0 mm and a radius of curvature less than 50 mm;
    said lead member and said electrode main body being bonded together at connecting portions thereof by electroconductive adhesive, such as one of a thermosetting resin and rubber adhesive each of which is admixed with fine particles of carbon black, to form said electrode, the whole of said electrode being substantially transparent to X-rays.

2. An electrode as recited in claim 1, wherein said thermosetting resin is one of a phenol resin and an epoxy resin; and
    wherein said bonded connecting portions are calcined and carbonized at a temperature of not less than 1000° C. so as to decrease electrical resistance between said connecting portions.

3. an electrode according to claim 2, wherein said adhesive comprising a thermosetting resin having a content of carbon black in the range of 30 to 90 wt. %.

4. An electrode according to claim 2 wherein a sponge-like porous buffering material impregnated with an electrolyte solution is provided at said living body contact surface of said electrode main body.

* * * * *